United States Patent [19]
Effland et al.

[11] Patent Number: 5,856,335
[45] Date of Patent: *Jan. 5, 1999

[54] SUBSTITUTED AMINOTHIENOPYRIDINES, PHARMACEUTICAL COMPOSITION AND USE

[75] Inventors: Richard Charles Effland; Joseph Thomas Klein, both of Bridgewater; Lawrence Leo Martin, Lebanon, all of N.J.

[73] Assignee: Hoechst Marion Roussel, Inc., Cincinnati, Ohio

[ * ] Notice: The term of this patent shall not extend beyond the expiration date of Pat. No. 5,

[21] Appl. No.: 780,525

[22] Filed: Jan. 8, 1997

Related U.S. Application Data

[60] Continuation of Ser. No. 451,585, May 26, 1995, abandoned, which is a division of Ser. No. 132,731, Oct. 6, 1993, Pat. No. 5,519,032, which is a division of Ser. No. 917,247, Jul. 20, 1992, Pat. No. 5,252,581.

[51] Int. Cl.$^6$ .................... C07D 471/04; C07D 487/04; A61K 31/44
[52] U.S. Cl. ............................................. 514/301; 546/114
[58] Field of Search ............................... 546/114; 514/301

[56] References Cited

U.S. PATENT DOCUMENTS

| | | | |
|---|---|---|---|
| 2,811,527 | 10/1957 | Sheehan | 514/114 |
| 3,952,989 | 4/1976 | Kuwada et al. | 248/453 |
| 5,026,698 | 6/1991 | Fujikawa et al. | 514/215 |
| 5,252,581 | 10/1993 | Effland et al. | 514/301 |

FOREIGN PATENT DOCUMENTS 2440738  6/1980  France .

OTHER PUBLICATIONS

Dunn, et al., J. Heterocyclic Chem. 24:85–89 (1987).
Barker, et al., J. Chem. Research (S) 4:122–123 (1986).
Klemm et al., J. of Het. Chem., vol. 7, pp. 373–379 (1970).
Klemm et al., J. of Het. Chem. vol. 12, pp. 1183–1186 (1975).
Klemm, et al., J. of Het. Chem., vol. 14, pp. 290–303 (1977).
Guerra et al., Framaco, Ed. Sci., vol. 32, pp. 249–268 (1970).
Gronowitz et al., Arkiv For. Kemi, vol. 32, pp. 249–268 (1970).
Horn, J. of Neurochemistry, vol. 21, pp. 883–888 (1973).
Fiegliner, J. of Clinical Psychopharmacology, Suppli., vol. 1, pp. 23S–26S (1981).
Traber, et al., Trends in Pharmacological Sciences, vol. 8, pp. 432–437 (1987).

*Primary Examiner*—Alan L. Rotman
*Attorney, Agent, or Firm*—Balaram Gupta

[57] ABSTRACT

This application relates to compounds of the formula

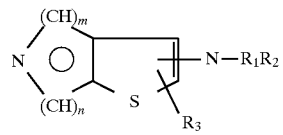

wherein $R^1$, $R^2$, $R^3$, m and n are as defined in the specification which are useful as modulators of neurotransmitter function such as serotonergic and adrenergic, and as such are useful as antidepressants, anxiolytics, atypical antipsychotics, antiemetics, and for the treatment of personality disorders such as obsessive compulsive disorders. Certain of the compounds are also useful as glycine partial agonists.

25 Claims, No Drawings

SUBSTITUTED AMINOTHIENOPYRIDINES, PHARMACEUTICAL COMPOSITION AND USE

This is a continuation, of application Ser. No. 08/451,585, filed May 26, 1995, now abandoned which is a divisional of Ser. No. 07/132,731, filed Oct. 6, 1993, now U.S. Pat. No. 5,519,032, which is a divisional of Ser. No. 07/917,247, filed Jul. 20, 1992, now U.S. Pat. No. 5,252,581, which are herein incorporated by reference.

The present invention relates to compounds of the formula,

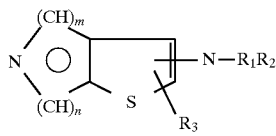

where $R^1$ is hydrogen, $(C_1-C_6)$alkyl, $(C_3-C_6)$alkenyl, $(C_3-C_6)$alkynyl, aryl$(C_1-C_6)$alkyl, $(C_1-C_6)$alkylcarbonyl, formyl, $(C_1-C_6)$alkoxycarbonyl, aryl$(C_1-C_6)$alkoxycarbonyl, aryl$(C_1-C_6)$alkoxycarbonylamino$(C_{1-18})$alkylcarbonyl, $(C_1-C_6)$alkoxycarbonylamino$(C_1-C_{18})$alkylcarbonyl, $(C_1-C_6)$alkylamino$(C_1-C_6)$alkylcarbonyl, amino$(C_1-C_{18})$alkylcarbonyl, $(C_1-C_6)$dialkylamino$(C_1-C_6)$alkylcarbonyl, amino$(C_1-C_6)$alkyl, $(C_1-C_6)$alkylamino$(C_1-C_6)$alkyl, or $(C_1-C_6)$dialkylamino$(C_1-C_6)$alkyl;

$R^2$ is hydrogen, $(C_1-C_6)$alkyl or

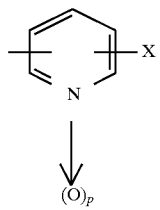

with the proviso that $R^1$ and $R^2$ are not concurrently hydrogen; and $R^3$ is hydrogen, $(C_1-C_6)$alkyl or $(C_1-C_6)$alkoxycarbonyl; where X is hydrogen, $(C_1-C_6)$alkyl, halo, $(C_1-C_6)$alkoxy or nitro;

n is 0, 1, 2 or 3;

m is 0, 1, 2 or 3; with the proviso that the sum of m and n is always 3; and p is 0 or 1; and pharmaceutically acceptable addition salts thereof and optical or geometrical isomers or racemic mixtures thereof;

which compounds are useful as modulators of neurotransmitter function such as serotonergic and adrenergic, and as such are useful as antidepressants, anxiolytics, atypical antipsychotics, antiemetics, and for the treatment of personality disorders such as obsessive compulsive disorders. Certain of the compounds are also useful as glycine partial agonists. This invention also relates to pharmaceutical compositions containing these compounds, methods of their use and a process for making these compounds.

Unless otherwise stated or indicated, the following definitions shall apply throughout the specification and the appended claims.

The term $(C_1-C_6)$alkyl and $(C_1-C_{18})$alkyl shall mean a straight or branched alkyl group, for example, methyl, ethyl, n-propyl, iso-propyl, n-butyl, iso-butyl, sec-butyl, t-butyl and straight- and branched-chain pentyl and hexyl, and, in the case of $(C_1-C_{18})$alkyl optionally substituted by hydroxymethyl or trifluoromethyl.

The term halo(halogen) shall mean fluorine, chlorine, bromine or iodine.

The term aryl shall mean a phenyl group substituted with 0, 1 or 2 substituents each of which being independently $(C_1-C_6)$alkyl, $(C_1-C_6)$alkoxy, halogen, nitro or trifluoromethyl.

Throughout the specification and the appended claims, a given chemical formula or name shall encompass all stereo, optical and tautomeric isomers where such isomers exist.

In one class of compounds of this invention are compounds of the formula

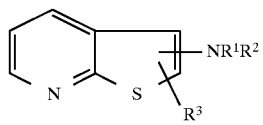

(II)

wherein $R^1$, $R^2$ and $R^3$ are as defined above.

In one preferred embodiment of this class are compounds of the formula

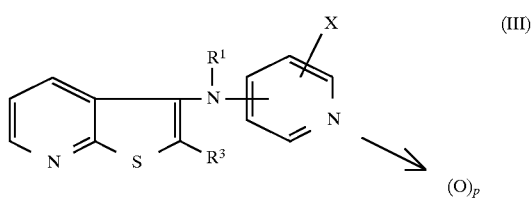

(III)

wherein $R^1$ is hydrogen, $(C_1-C_6)$alkyl, $(C_3-C_6)$alkenyl, $(C_3-C_6)$alkynyl, aryl$(C_1-C_6)$alkyl, $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl, $(C_1-C_6)$alkoxycarbonyl, amino$(C_1-C_{18})$alkylcarbonyl, $(C_1-C_6)$alkylcarbonyl, amino$(C_1-C_6)$alkyl or $(C_1-C_6)$alkylamino$(C_1-C_6)$alkyl; and $R^3$ is hydrogen, $(C_1-C_6)$alkyl or $(C_1-C_6)$alkoxycarbonyl; where X is hydrogen, $(C_1-C_6)$alkyl, halo or nitro; and p is 0 or 1.

More preferably, in this embodiment $R^1$ is hydrogen, $C_1-C_6$ alkyl or $(C_1-C_6)$alkylcarbonyl;

$R^3$ is hydrogen or $(C_1-C_6)$alkoxycarbonyl;

X is hydrogen; and p is 0.

Most preferably, the compounds have the formula

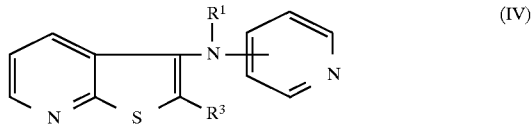

(IV)

where $R^1$ is hydrogen, $(C_1-C_6)$alkyl or $(C_1-C_6)$alkylcarbonyl; and $R^3$ is hydrogen.

In another embodiment of this class are compounds of the formula

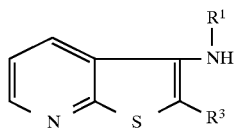
(V)

wherein $R^1$ is $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl, amino$(C_1-C_{18})$alkylcarbonyl, $(C_1-C_6)$alkylamino$(C_1-C_6)$alkylcarbonyl or $(C_1-C_6)$dialkylamino$(C_1-C_6)$alkylcarbonyl; and $R^3$ is hydrogen.

Most preferably, $R^1$ is $(C_1-C_6)$alkoxycarbonylamino$(C_1)$alkylcarbonyl or amino$(C_1)$alkylcarbonyl.

In another class of compounds of this invention are compounds of the formula

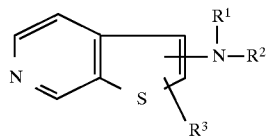
(VI)

wherein $R^1$, $R^2$ and $R^3$ are as defined above.

In a preferred embodiment of this class are compounds of the formula

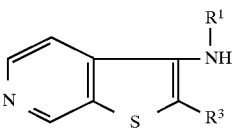
(IX)

wherein $R^1$ is $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl or amino$(C_1-C_{18})$alkylcarbonyl and $R^3$ is hydrogen.

Most preferably, $R^1$ is $(C_1-C_6)$alkoxycarbonylamino$(C_1)$alkylcarbonyl or amino$(C_1)$alkylcarbonyl.

In another class of compounds of this invention are compounds of the formula

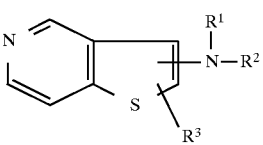
(X)

wherein $R^1$, $R^2$ and $R^3$ are as defined above.

In a preferred embodiment of this class are compounds of the formula

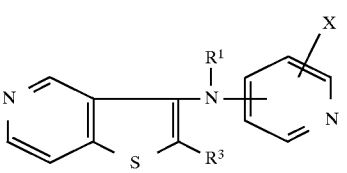
(VII)

wherein $R^1$ is hydrogen, $(C_1-C_6)$alkyl, $(C_3-C_6)$alkenyl, $(C_3-C_6)$alkynyl, aryl$(C_1-C_6)$alkyl, $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl, $(C_1-C_6)$alkoxycarbonyl, amino$(C_1-C_{18})$alkylcarbonyl, $(C_1-C_6)$alkylcarbonyl, amino$(C_1-C_6)$alkyl or $(C_1-C_6)$alkylamino$(C_1-C_6)$alkyl; and $R^3$ is hydrogen, $(C_1-C_6)$alkyl or $(C_1-C_6)$alkoxycarbonyl;

where X is hydrogen, $(C_1-C_6)$alkyl, halo or nitro; and p is 0 or 1.

More preferably, in this embodiment $R^1$ is hydrogen, $(C_1-C_6)$ or $(C_1-C_6)$alkylcarbonyl; $R^3$ is hydrogen or $(C_1-C_6)$alkoxycarbonyl; X is hydrogen; and p is 0.

Most preferably, the compounds have the formula

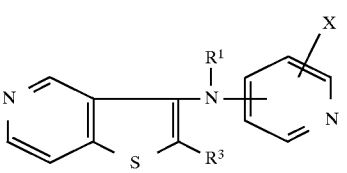
(XI)

wherein $R^1$ is hydrogen, $(C_1-C_6)$alkyl, $(C_3-C_6)$alkenyl, $(C_3-C_6)$alkynyl, aryl$(C_1-C_6)$alkyl, $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl, $(C_1-C_6)$alkoxycarbonyl, amino$(C_1-C_{18})$alkylcarbonyl, $(C_1-C_6)$alkylcarbonyl, amino$(C_1-C_6)$alkyl or $(C_1-C_6)$alkylamino$(C_1-C_6)$alkyl; and $R^3$ is hydrogen, $(C_1-C_6)$alkyl or $(C_1-C_6)$alkoxycarbonyl;

where X is hydrogen, $(C_1-C_6)$alkyl, halo or nitro; and p is 0 or 1.

More preferably in this embodiment $R^1$ is hydrogen, $(C_1-C_6)$alkyl or $(C_1-C_6)$alkylcarbonyl; $R^3$ is hydrogen or $(C_1-C_6)$alkoxycarbonyl; X is hydrogen; and p is 0.

Most preferably, the compounds have the formula

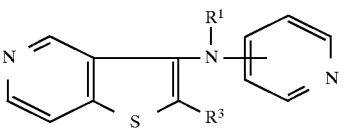
(VIII)

where $R^1$ is hydrogen, $(C_1-C_6)$ or $(C_1-C_6)$alkylcarbonyl; and $R^3$ is hydrogen.

In another embodiment of this class are compounds of the formula

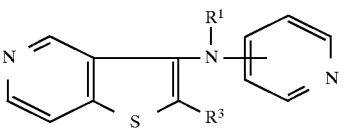
(XII)

where $R^1$ is hydrogen, $(C_1-C_6)$alkyl or $(C_1-C_6)$alkylcarbonyl; and $R^3$ is hydrogen.

In another embodiment of this class are compounds of the formula (XIII)

wherein $R^1$ is $(C_1-C_6)$alkoxycarbonylamino$(C_1-C_{18})$ alkylcarbonyl, aryl$(C_1-C_6)$alkoxycarbonylamino$(C_1-C_{18})$alkylcarbonyl or amino$(C_1-C_{18})$ alkylcarbonyl and $R^3$ is hydrogen.

Most preferably, $R^1$ is $(C_1-C_6)$alkoxycarbonylamino$(C_1)$ alkylcarbonyl or amino$(C_1)$alkylcarbonyl.

In yet another class of compounds of this invention are compounds of the formula (XIV)

wherein $R^1$, $R^2$ and $R^3$ are as defined above.

In a preferred embodiment of this call are compounds of the formula (XV)

wherein $R^1$ is hydrogen, $(C_1-C_6)$alkyl, $(C_3-C_6)$alkenyl, $(C_3-C_6)$ alkynyl, aryl$(C_1-C_6)$alkyl, $(C_1-C_6)$ alkoxycarbonylamino$(C_1-C_{18})$alkylcarbonyl, aryl $(C_1-C_6)$alkoxycarbonylamino$(C_1-C_{18})$alkylcarbonyl, $(C_1-C_6)$alkoxycarbonyl, amino$(C_1-C_{18})$alkylcarbonyl, $(C_1-C_6)$alkylcarbonyl, amino$(C_1-C_6)$alkyl or $(C_1-C_6)$ alkylamino$(C_1-C_6)$alkyl; and $R^3$ is hydrogen, $(C_1-C_6)$alkyl or $(C_1-C_6)$alkoxycarbonyl;

where X is hydrogen, $(C_1-C_6)$alkyl, halo or nitro; and p is 0 or 1.

More preferably in the embodiment $R^1$ is hydrogen, $(C_1-C_6)$alkyl or $(C_1-C_6)$alkylcarbonyl;

$R^3$ is hydrogen or $(C_1-C_6)$alkoxycarbonyl;

X is hydrogen; and p is 0.

Most preferably, the compounds have the formula (XVI)

where $R^1$ is hydrogen, $(C_1-C_6)$alkyl or $(C_1-C_6)$ alkylcarbonyl; and $R^3$ is hydrogen.

In another embodiment of this class are compounds of the formula (XVII)

wherein $R^1$ is $(C_1-C_6)$alkoxycarbonylamino$(C_1-C_{18})$ alkylcarbonyl, aryl$(C_1-C_6)$alkoxycarbonylamino $(C_1-C_{18})$alkylcarbonyl or amino$(C_1-C_{18})$ alkylcarbonyl and $R^3$ is hydrogen.

Most preferably, $R^1$ is $(C_1-C_6)$alkoxycarbonylamino$(C_1)$ alkylcarbonyl or amino$(C_1)$alkylcarbonyl.

Nonlimiting examples of compounds of this invention include:
3-(4-pyridinylamino)thieno[2,3-b]pyridine;
3-(propyl-4-pyridinylamino)thieno[2,3-b]pyridine;
3-(methyl-4-pyridinylamino)thieno[2,3-b]pyridine;
3-(ethyl-4-pyridinylamino)thieno[2,3-b]pyridine;
3-(butyl-4-pyridinylamino)thieno[2,3-b]pyridine;
3-(4-pyridinylamino)thieno[3,2-c]pyridine;
3(propyl-4-pyridinylamino)thieno[3,2-c]pyridine;
3-(methyl-4-pyridinylamino)thieno[3,2-c]pyridine;
3-(ethyl-4-pyridinylamino)thieno[3,2-c]pyridine;
3-(butyl-4-pyridinylamino)thieno[3,2-c]pyridine;
3-(4-pyridinylamino)thieno[3,2-b]pyridine;
3-(propyl-4-pyridinylamino)thieno[3,2-b]pyridine;
3-(methyl-4-pyridinylamino)thieno[3,2-b]pyridine;
3-(ethyl-4-pyridinylamino)thieno[3,2-b]pyridine;
3-(butyl-4-pyridinylamino)thieno[3,2-b]pyridine;
3-(4-pyridinylamino)thieno[2,3-c]pyridine;
3-(methyl-4-pyridinylamino)thieno[2,3-c]pyridine;
3-(ethyl-4-pyridinylamino)thieno[2,3-c]pyridine;
3-(propyl-4-pyridinylamino)thieno[2,3-c]pyridine;
3-(butyl-4-pyridinylamino)thieno[2,3-c]pyridine;
3-(acetyl-4-pyridinylamino)thieno[2,3-c]pyridine;
3-(acetyl-4-pyridinylamino)thieno[2,3-b]pyridine;
3-(propionyl-4-pyridinylamino)thieno[2,3-b]pyridine;
3-(acetyl-4-pyridinylamino)thieno[3,2-c]pyridine;
3-(propionyl-4-pyridinylamino)thieno[3,2-c]pyridine;
3-(acetyl-4-pyridinylamino)thieno[3,2-b]pyridine;
3-(propionyl-4-pyridinylamino)thieno[2,3-b]pyridine;
3-(propionyl-4-pyridinylamino)thieno[2,3-c]pyridine;
2-amino-N-(thieno[2,3-b]pyridin-3-yl)acetamide;
2-amino-N-(thieno[3,2-c]pyridin-3-yl)acetamide;
2-amino-N-(thieno[3,2-b]pyridin-3-yl)acetamide;
2-amino-N-(thieno[2,3-c]pyridin-3-yl)acetamide;
t-butyl[2-(thieno[2,3-b]pyridin-3-ylamino)-2-oxoethyl] carbamate;
t-butyl[2-(thieno[3,2-c]pyridin-3-ylamino)-2-oxoethyl] carbamate;
t-butyl[2-(thieno[3,2-b]pyridin-3-ylamino)-2-oxoethyl] carbamate;
t-butyl [2-(thieno[2,3-c]pyridin-3-ylamino)-2-oxoethyl] carbamate;

The compounds of the invention are prepared by one or more of the synthetic routes described below.

Throughout the description of the synthetic schemes, the notations $R^1$, $R^3$, X, m, n and p have the respective meanings given above unless otherwise stated or indicated and other notations have the respective meanings defined in their first appearances.

More particularly, as shown in Reaction Scheme A, an aminothienopyridine of Formula XVIII is reacted with a halopyridine of Formula XIX or the compound of Formula XX wherein $R^4$ is hydrogen, $(C_1-C_6)$alkyl or hydroxy $(C_1-C_6)$alkyl, $R^5$ is hydrogen or $(C_1-C_6)$alkyl, $R^6$ is hydrogen or $(C_1-C_6)$alkyl, $R^7$ is $(C_1-C_6)$alkyl or aryl$(C_1-C_6)$alkyl and k and q are independently 0 to 5 with the proviso that the sum of k and q is not greater than 5, to obtain the N-substituted compound of Formula XXI or XXII, respectively.

about 15° C. to about 80° C., most preferably from about 20° C. to about 50° C.

The compound of Formula XXII is deprotected by means known in the art. In the case where $R^7$ is phenylmethyl, the compound of Formula XXII is deprotected, for example, by treatment with hydrogen in the presence of a catalyst such as

REACTION SCHEME A

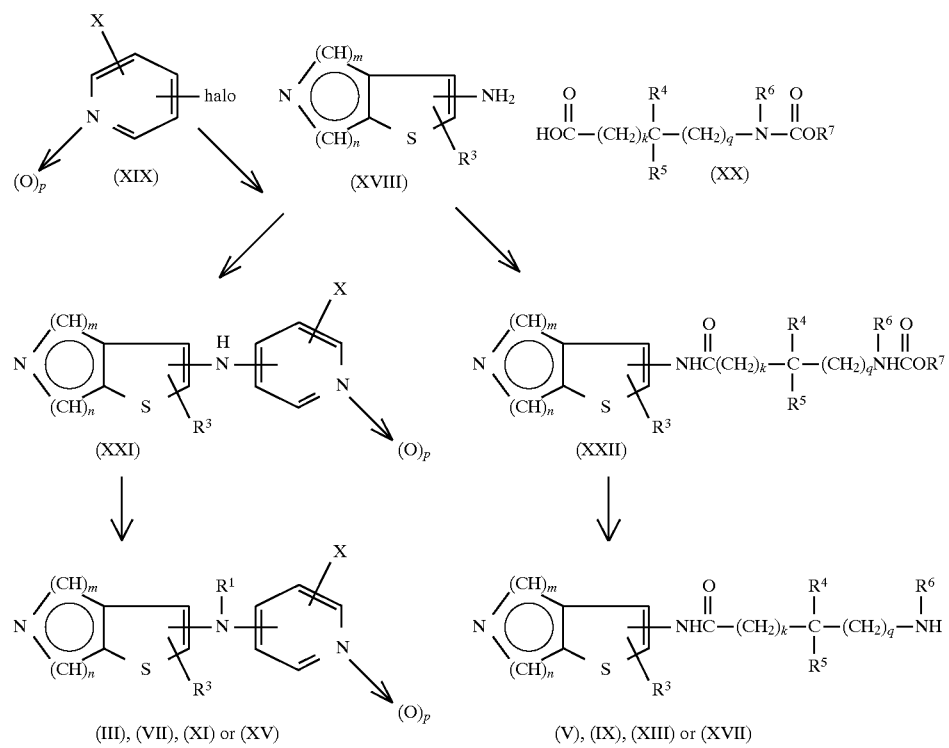

When the product is the compound of Formula XXI on Scheme A, the reaction is generally carried out in an ethereal solvent such as bis(2-methoxyethyl)ether, diethyl ether, dimethoxyethane, dioxane or tetrahydrofuran or a polar aprotic solvent such as dimethylformamide, dirnethylacetamide, N-methyl-2-pyrrolidone, hexamethylphosphoramide or dimethyl sulfoxide or polar solvent such as ethanol or isopropanol at a temperature of between about 0° C. and 200° C., preferably between about 20° C. and 150° C., most preferably between about 50° C. and 100° C.

The compound of Formula XXI is then allowed to react with a halide or sulfate of the formula $R^8$hal where $R^8$ is $(C_1-C_6)$alkyl, $(C_3-C_6)$alkenyl, $(C_3-C_6)$alkynyl or aryl $(C_1-C_6)$alkyl, or $(R^9O)_2SO_2$ where $R^9$ is $(C_1-C_6)$alkyl, at a temperature of from about -10° C. to about 80° C., preferably from about 0° C. to about 25° C. to obtain the compound of Formula III, VII, XI or XV where $R^1$ corresponds to $R^8$ or $R^9$ above.

In the case where the product is the compound of Formula XXII the reaction is carried out in the presence of a condensing agent such as dicyclohexylcarbodiimide (DCC.). Typically, the reaction is carried out in a suitable solvent such as an aprotic organic solvent, for example, dichloromethane, dioxane or tetrahydrofuran at a temperature of from about 0° C. to about 100° C., preferably from palladium on carbon to yield the amino compound of Formula V, IX, XIII or XVII. The reaction is typically carried out in a polar solvent such as methanol or ethanol at about 10° C. to 50° C., preferably from about 15° C. to about 30° C.

When $R^7$ of Formula XXII is t-butyl, the compound is deprotected by means known in the art, for example, by treatment with acid such as hydrochloric acid, hydrobromic acid or trifluoroacetic acid in an organic solvent such as ethyl acetate, tetrahydrofuran, methanol, chloroform and the like, or neat, at from about -50° C. to about 100° C. Preferably, the reaction is carried out in the presence of hydrochloric acid in methanol at about -15° C. to about 30° C.

The aminothienopyridine starting materials are prepared according to methods known in the art, for example, reaction of the appropriate cyanohalopyridine with methylthioglycolate (*J. Het. Chem.*, 24 85 (1987), *J. Het. Chem.*, 7 373 (1970)) followed by removal of the 2-ester group as outlined in Reaction Scheme B for 3-aminothieno[2,3-b]pyridine and 3-aminothieno[2,3-c]pyridine. The starting pyridine compound 3-chloro-4-cyanopyridine can be prepared from 4-cyanopyridine N-oxide by means known in the art (*J. Het. Chem.*, 15 683 (1978)).

REACTION SCHEME B

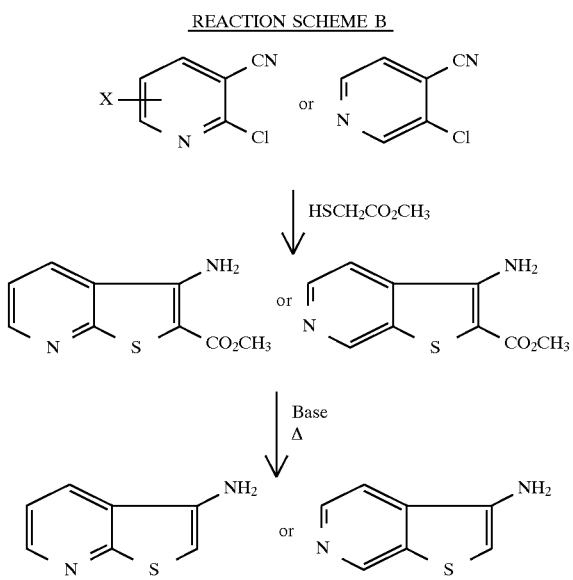

The compounds of Formula III, V, VII, IX, XI, XIII, XV and XVII of the present invention are useful as modulators of neurotransmitter function such as serotonergic and adrenergic and, as such, are useful as antidepressants, anxiolytics, atypical antipsychotics, antiemetics, and for the treatment of personality disorders such as obsessive compulsive disorders. Certains of the compounds are also useful as glycine partial agonists.

[$^3$H]-8-Hydroxy-2-(di-n-propylamino)-tetralin ([$^3$H] DPAT) Binding to Serotonin (5HT$_{1A}$) Receptors Purpose:

The purpose of this assay is to determine the affinity of test compounds for the 5HT$_{1A}$ receptor in brain. It is believed to be useful for predicting compounds with serotonergic properties with potential utility as novel anxiolytics (1–4), atypical antipsychotics or useful in the treatment of personality disorders such as obsessive compulsive disorder.

Introduction

The existence of two populations of 5HT receptors in rat brain was shown by differential sensitivity to spiroperidol (5). The spiroperidol-sensitive receptors were designated as the 5HT$_{1A}$ subtype and the insensitive receptors were referred to as the 5HT$_{1B}$ subtype (6). Other 5HT binding sites (5HT$_{1C}$, 5HT$_{1D}$ and 5HT$_3$) have subsequently been identified in various species, based on differential sensitivity to 5HT antagonists (7). A significant advance in the classification of 5HT receptors came with the identification of a selective ligand for the $^5$HT$_{1A}$ receptor, [$^3$H]DPAT (8). These authors reported that [$^3$H]DPAT labeled an autoreceptor. Lesion studies suggest that [$^3$H]DPAT labeled receptors are not terminal autoreceptors, but may be somatodendritic autoreceptors (9)). Although DPAT decreases the firing rate in the Raphe nucleus and inhibits 5HT release, the actual location and function is somewhat controversial (2). These studies and the sensitivity of [$^3$H]DPAT binding to guanine nucleotides and effects on adenylate cyclase suggest that DPAT acts as an agonist at the 5HT$_{1A}$ receptor (10).

Procedure I:

A. Reagents

Tris Buffers, pH7.7

(a) 57.2 g Tris HCl
  16.2 g Tris base
  Bring volume to 1 liter with distilled water (0.5M Tris buffer, pH 7.7).

(b) Make a 1:10 dilution in deionized H$_2$O (0.05M Tris buffer, pH 7.7).

(c) 0.05M Tris buffer, pH 7.7 containing 10 μM pargyline, 4 mM CaCl$_2$ and 0.1% ascorbic acid.
  0.49 mg pargyline•HCl
  111 mg CaCl$_2$
  250 ascorbic acid
  Bring to 250 ml with 0.05M Tris buffer, pH 7.7 (reagent 1b)

2. 8-Hydroxy[$^3$H]-DPAT (2-(N,N-Di[2,3(n)-$^3$H] propylamino)-8-hydroxy-1,2,3,4-tetrahydronaphthalene) (160–206 Ci/mmol) was obtained from Amersham.

For IC$_{50}$ determinations: a 10 nM stock solution is made up and 50 μl added to each tube (final concentration=0.5 nM).

3. Serotonin creatinine sulfate. 0.5 mM stock solution is made up in 0.01N HCl and 20 μl added to 3 tubes for determination of nonspecific binding (final concentration= 10 μM).

4. Test Compounds. For most assays, a 1 mM stock solution is made up in a suitable solvent and serially diluted, such that the final concentration in the assay ranges from $2 \times 10^5$ to $2 \times 10^{-8}$ M. Seven concentrations are used for each assay. Higher or lower concentrations may be used based on the potency of the drug.

B. Tissue Preparation

Male Wistar rats are sacrificed by decapitation. Hippocampi are removed, weighed and homogenized in 20 volumes of 0.05M Tris buffer, pH 7.7. The homogenate is centrifuged at 48,000 g for 10 minutes and the supernatant is discarded. The pellet is resuspended in an equal volume of 0.05M Tris buffer, incubated at 37° C. for 10 minutes and recentrifuged at 48,000 g for 10 minutes. The final membrane pellet is resuspended in 0.05M Tris buffer containing 4 mM CaCl$_2$, 0.1% ascorbic acid and 10 μM pargyline.

C. Assay
  800 μl Tissue
  130 μl 0.05M Tris+CaCl$_2$+pargyline+ascorbic acid
  20 μl vehicle/5HT/drug
  50 μl [$^3$H]DPAT Tubes are incubated for 15 minutes at 25° C. The assay is stopped by vacuum filtration through Whatman GF/B filters which are then washed 2 times with 5 ml of ice-cold 0.05M Tris buffer. The filters are then placed into scintillation vials with 10 ml of Liquiscint scintillation cocktail and counted.

Calculation

Specific binding is defined as the difference between total binding and binding in the presence of 10 μM 5HT. IC$_{50}$ values are calculated from the percent specific binding at each drug concentration.

Procedure II:

A. Reagents

1. Tris Buffers, pH 7.7

(a) 57.2 g Tris HCl
  16.2 g Tris base
  Bring to 1 liter with distilled water (0.5M Tris buffer, pH 7.7).

(b) Make a 1:10 dilution in distilled H$_2$O (0.05M Tris buffer, pH 7.7 at 25° C.).

(c) 0.05M Tris buffer, pH 7.7 containing 10 μM pargyline, 4 mM CaCl$_2$ and 0.1% ascorbic acid.
  0.49 mg pargyline•HCl
  110.99 mg CaCl$_2$
  250 ascorbic acid
  Bring to 250 ml with 0.05M Tris buffer, pH 7.7 (reagent 1b).

2. 8-Hydroxy[$^3$H]-DPAT (2-N,N-Di[2,3(n)-$^3$H] propylamino)-8-hydroxy-1,2,3,4-tetrahydronaphthalene)] (160–206 Ci/mmol) is obtained from Amersham.

For IC$_{50}$ determinations: $^3$H-DPAT is made up to a concentration of 3.3 nM in the Tris Buffer (1c) such that when 150 μl is added to each tube a final concentration of 0.5 nM is attained in the 1 ml assay.

3. Serotonin creatinine sulfate is obtained from the Sigma Chemical Company. Serotonin creatinine sulfate is made up to a concentration of 100 μM in Tris buffer (1c). One hundred μl is added to each of 3 tubes for the determination of nonspecific binding (this yields a final concentration of 10 μM in the 1 ml assay).

4. Test Compounds. For most assays, a 100 μM stock solution is made up in a suitable solvent and serially diluted with Tris buffer (1c) such that when 100 μl of drug is combined with the total 1 ml assay, a final concentration ranging from 10$^{-5}$ to 10$^{-8}$M is attained. Characteristically seven concentrations are studied for each assay; however, higher or lower concentrations may be used, depending on the potency of the drug.

B. Tissue Preparation

Male Wistar rats are decapitated, the hippocampi are removed and homogenized in 20 volumes of ice cold 0.05M Tris buffer, pH 7.7 (1b). The homogenate is centrifuged at 48,000 g for 10 minutes at 4° C. The resulting pellet is rehomogenized in fresh Tris buffer (1b), incubated at 37° C. for 10 minutes and recentrifuged at 48,0000 g for 10 minutes. The final membrane pellet is resuspended in 0.05M Tris buffer (1c) containing 4 mM CaCl$_2$, 0.1% ascorbic acid and 10 μM pargyline. Specific binding is approximately 90% of total bound ligand.

C. Assay

750 μl Tissue
150 μl [$^3$H]DPAT
100 μl vehicle (for total binding) or 100 μM serotonin creatinine sulfate (for nonspecific binding) or appropriate drug concentration Tubes are incubated for 15 minutes at 25° C. The assay is stopped by vacuum filtration through Whatman GF/B filters which are then washed 2 times with 5 ml of ice-cold 0.05M Tris buffer (1b). The filters are then placed into scintillation vials with 10 ml of Liquiscint scintillation cocktail and counted. Specific binding is defined as the difference between total binding in the absence or presence of 10 μM serotonin creatinine sulfate. IC$_{50}$ values are calculated from the percent specific binding at each drug concentration.

The K$_D$ value for [$^3$H] DPAT binding was found to be 1.3 nM by Scatchard analysis of a receptor saturation experiment. The K$_i$ value may then be calculated by the Cheng-Prusoff equation:

$$K_i = IC_{50}/1 + L/K_D$$

References:
1. Dourish C. T., Hutson, P. H. and Curzon, G.: Putative anxiolytics 8-OH-DPAT, buspirone and TVX Q 7821 are agonists at 5 HT$_{1A}$ autoreceptors in the raphe nucleus. TIPS 7: 212–214(1986).
2. Verge, D., Daval, G., Marcinkiewicz, M., Patey, A., El Mestikawy, H. Gozlan and Hamon, M.: Quantitative autoradiography of multiple 5-HT$_1$ receptor subtypes in the brain of control or 5,7,dihydroxytryptamine-treated rats. J. Neurosci. 6: 3474–3482 (1986).
3. Iversen, S. D.: 5HT and anxiety. Neuropharmacol. 23: 1553–1560 (1984).
4. Traber J. and Glaser, T.:5HT$_{1A}$ receptor-related anxiolytics. TIPS 8: 432–437 (1987).
5. Pedigo, N. W., Yammamura, H. I. and Nelson, D. L.: Discrimination of multiple [$^3$H]5-hydroxytryptamine binding sites by the neuroleptic spiperone in rat brain. J. Neurochem. 36: 220–226 (1981).
6. Middlemiss, D. N. and Fozard J. R.: 8-Hydroxy-2-(di-n-propylamino)tetraline discriminates between subtypes of the 5HT$_1$ recognition site. Eur. J. Pharmacol. 90: 151–152 (1983).
7. Peroutka, S. J.: Pharmacological differentiation and characterization of 5-HT$_{1A}$, 5-HT$_{1B}$ and 5-HT$_{1C}$ binding sites in rat frontal cortex. J. Neurochem. 47: 529–540 (1986).
8. Peroutka, S. J.: 5-Hydroxytryptamine receptor subtypes: molecular, biochemical and physiological characterization TINS 11: 496–500 (1988).
9. Gozlan, H., El Mestikawy, S., Pichat, L. Glowinsky, J. and Hamon, M.: Identification of presynaptic serotonin autoreceptors using a new ligand: $^3$H-PAT. Nature 305: 140–142 (1983).
10. Schlegel,.R. and Peroutka, S. J.: Nucleotide interactions with 5-HT$_{1A}$ binding sites directly labeled by [$^3$H]-8-hydroxy-2-(di-n-propylamino)tetralin ([$^3$H]-8-OH-DPAT). Biochem. Pharmacol. 35: 1943–1949 (1986).
11. Peroutka, S. J.: Selective interaction of novel anxiolytics with 5-hydroxytryptamine$_{1A}$ receptors. Biol. Psychiatry. 20: 971–979(1985).

$^3$H-Serotonin Uptake in Rat Whole Brain Synaptosomes

Purpose:

This assay is used as a biochemical screen for potential antidepressants which block serotonin (5HT) uptake, which may be useful for the treatment of personality disorders such as obsessive compulsive disorder.

Introduction:

Asberg and coworkers have suggested that subjects with serotonergic hypofunction comprise a biochemical subgroup of depressed patients (1), while others (2) claim that altered serotonergic function determines the mood changes associated with affective disorders. Although the role of 5HT in the etiology of depression is not clear; it is true that a number of antidepressant drugs block the 5HT uptake mechanism. In vitro receptor binding assays have shown that [$^3$H]-imipramine labels 5HT uptakes sites (10). Trazodone and zimelidine are clinically effective antidepressants (3) with fairly selective effects on 5HT uptake (4,5). More recently, fluoxetine has been shown to be both a selective and potent 5HT uptake inhibitor.

[$^3$H]-5HT transport has been characterized in CNS tissue (6,7) and found to be saturable, sodium- and temperature-dependent, inhibited by ouabain, metabolic inhibitors, tryptamine analogs (8) and tricyclic antidepressants (tertiary amines>>secondary amines) (9). The latter findings differentiate 5HT uptake from catecholamine uptake. [$^3$H]-5HT uptake can also be used as a marker for serotonin nerve terminals.

Procedure:

A. Animals: Male CR Wistar rats (100–125 g).
B. Reagents
1. Krebs-Henseleit Bicarbonate Buffer, pH 7.4 (KHBB): Make a 1 liter batch, containing the following salts.

|  | g/L | mM |
|---|---|---|
| NaCl | 6.92 | 118.4 |
| KCl | 0.35 | 4.7 |
| MgSO$_4$.7H$_2$O | 0.29 | 1.2 |

-continued

|  | g/L | mM |
|---|---|---|
| $KH_2PO_4$ | 0.16 | 2.2 |
| $NaHCO_3$ | 2.10 | 24.9 |
| $CaCl_2$ | 0.14 | 1.3 |
| Prior to use add: | | |
| Dextrose | 2 mg/ml | 11.1 |
| Iproniazid phosphate | 0.30 mg/ml | 0.1 |

Aerate for 60 min. with 95% $O_2$/5% $CO_2$, check pH (7.4±0.1)

2. 0.32M Sucrose: 21.9 g of sucrose, bring to 200 ml.
3. Serotonin creatinine $SO_4$ is obtained from Sigma Chemical Co. A 0.1 mM stock solution is made up in 0.01N HCl . This is used to dilute the specific activity of radiolabeled 5HT.
4. 5-[1,2-$^3$H(N)]-Hydroxytryptamine creatinine sulfate (Serotonin), specific activity 20–30 Ci/mmol is obtained from New England Nuclear.

The final desired concentration of $^3$H-5HT in the assay is 50 nM. The dilution factor is 0.8 Therefore, the KHBB is made up to contain 62.5 nM [$^3$H]-5HT.

Add to 100 ml of KHBB.

| A) 56.1 μl of 0.1 mM 5HT | = 56.1 nM |
|---|---|
| *B) 0.64 nmole of $^3$H-5HT | = 6.4 nM |
| | 62.5 nM |

*Calculate volume added from specific activity of $^3$H-5HT.

5. For most assays, a 1 mM solution of the test compound is made up in suitable solvent and serially diluted such that the final concentration in the assay ranges from $2\times10^{-8}$ to $2\times10^{-5}$M. Seven concentrations are used for each assay. Higher or lower concentrations may be used depending on the potency of the compound.

C. Tissue Preparation

Male Wistar rats are decapitated and the brain rapidly removed. Whole brain minus cerebella is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min. at 0°–4° C. The supernatant ($S_1$) is decanted and is used for uptake experiments.

D. Assay

800 μl KHBB+[$^3$H]-5HT
20 μl Vehicle or appropriate drug concentration
200 μl Tissue suspension Tubes are incubated at 37° C. under a 95% $O_2$/5% $CO_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

References:

1. Asberg, M., Thoren, P., Traskman, L., Bertilsson, L., and Ringberger, V. "Serotonin depression:-A biochemical subgroup within the affective disorders. Science 191: 478–480 (1975).
2. DeMontigy, C. Enhancement of 5HT neurotransmission by antidepressant treatments. J. Physiol. (Paris) 77: 455–461 (1980).
3. Feighner, J. P. Clinical efficacy of the newer antidepressants. J. Clin. Psychopharmacol. 1: 235–265 (1981).
4. Ogren, S. O., Ross, S. B., Hall, H., Holm, A. C. and Renyi, A. L. The pharmacology of zimelidine: A 5HT selective reuptake inhibitor. Acta Psychiat. Scand. 290: 127–151 (1981).
5. Clements-Jewry, S., Robson, P. A. and Chidley, L. J. Biochemical investigations into the mode of action of trazodone. Neuropharmacol. 19: 1165–1173 (1980).
6. Ross, S. B. Neuronal transport of 5-hydroxytryptamine. Pharmacol. 21: 123–131 (1980).
7. Shaskan, E. G. and Snyder, S. H. Kinetics of serotonin accumulation into slices from rat brain: Relationship to catecholamine uptake. J. Pharmacol. Exp. Ther. 175: 404–418 (1970).
8. Horn, S. A. Structure activity relations for the inhibition of 5HT uptake into rat hypothalamic homogenates by serotonin and tryptamine analogues. J. Neurochem. 21: 883–888 (1973).
9. Horn, A. S. and Trace, R. C. A. M. Structure-activity relations for the inhibition of 5-hydroxytryptamine uptake by tricyclic antidepressants into synaptosomes from serotonergic neurones in rat brain homogenates. Brit. J. Pharmacol. 51: 399–403 (1974).
10. Langer, S. Z., Moret, C., Raisman, R., Dubocovich, M. L. and Briley M. High affinity [$^3$H]imipramine binding in rat hypothalamus: Association with uptake of serotonin but not norepinephrine. Science 210: 1133–1135 (1980).

Results of the two assay methods described above are presented in Table I for representative compounds of this invention.

TABLE I

| | Inhibition of Biogenic Amine Reuptake $IC_{50}$ (μM) | | | $5HT_3$ Receptor |
|---|---|---|---|---|
| Compound | $^3$H-Serotonin (WB) | $^3$H-Norepinephrine (WB) | $^3$H-Dopamine (Str) | Binding Assay $IC_{50}$ (μM) |
| 3-(Propyl-4-pyridinylamino)-thieno[2,3-b]pyridine hydrochloride | 0.071 | 0.71 | 0.30 | 4.6 |
| 3-(Propyl-4-pyridinylamino)-thieno[2,3-c]pyridine | 0.54 | | | |
| Clomipramine | 0.033 | 0.36 | 31.5 | >10 | wb = whole brain;
str. = striatum

[³H]Glycine Binding

Purpose:

This assay is used to assess the affinity of compounds for the glycine binding site associated with the N-methyl-D-aspartate (NMDA) receptor complex using [³H]glycine as the radioligand.

Introduction:

The amino acid glycine modulates and may be a requirement for the activation of the excitatory amino acid receptors of the NMDA subtype (1). Glycine has been shown in vitro to potentiate the effects of 1-glutamate or NMDA on the stimulation of [³H]TCP binding (2,3,4) and [³H] norepinephrine release (5), and in vivo to act as a positive modulator of the glutamate-activated cGMP response in the cerebellum (6,7). The activation of NMDA receptors requiring the presence of glycine is necessary for the induction of long-term potentiation (LTP), a type of synaptic plasticity which may be fundamental to learning processes (8). A [³H]glycine binding site in the brain has been identified and characterized as a strychnine-insensitive site associated with the NMDA receptor complex (10, 11, 12). Autoradiographic studies have shown a similar distribution of [³H]glycine and [³H]TCP (NMDA ion channel radioligand) binding sites (13, 14). Compounds which interact with the glycine site offer a novel mechanism of action for intervention with NMDA receptor function.

Procedure:

A. Reagents

1. Buffer A: 0.5M Tris maleate, pH 7.4

59.3 g Tris maleate bring to 0.51 with distilled water Adjust pH to 7.4 with 0.5M Tris base.

2. Buffer B: 50 mM Tris maleate, pH 7.4

Dilute Buffer A 1:10 with distilled water; adjust pH with 50 mM Tris maleate (acid) or 50 mM Tris base.

3. Glycine, $5 \times 10^{-2}$M.

Dissolve 3.755 mg of glycine (Sigma G7126) with 1.0 ml distilled water. Aliquots of 20 µl to the assay tube will give a final concentration of $10^{-3}$M.

4. [³H]Glycine is obtained from New England Nuclear, specific activity 45–50 Ci/mmole. For $IC_{50}$ determinations, a 200 nM stock solution is made with distilled water. Aliquots of 50 µl are added to yield a final assay concentration of 10 nM.

5. Test compounds. A stock solution of 5 mM is made with a suitable solvent and serially diluted, such that the final concentration in the assay ranges from $10^{-4}$ to $10^{-7}$M. Higher or lower concentrations may be used, depending on the potency of the compound.

6. Triton-X 100, 10% (v/v) (National Diagnostics, EC-606). A stock solution of Triton-X 100, 10% can be prepared and stored in the refrigerator. Dilute 1.0 ml of Triton-X 100 to 10.0 ml with distilled water. On the day of the assay, the tissue homogenate (1:15 dilution) is preincubated with an aliquot of the 10% solution to give a final concentration of 0.04% (v/v).

B. Tissue Preparation

Cortices of male Wistar rats are dissected over ice and homogenized in ice-cold 0.32M sucrose (1:15 W/V) for 30 seconds with a Tissumizer setting at 70. Three cortices are pooled for one preparation. The homogenate is centrifuged at 1,000 g for 10 min (SS34, 3,000 rpm, 4° C.). The supernatant is centrifuged at 20,000 g (SS34, 12,000 rpm, 4° C.) for 20 minutes. The pellet is resuspended in 15 volumes of ice-cold distilled water (Tissumizer setting 70, 15 sec) and spun at 7,600 g (SS34, 8,000 rpm, 4° C.) for 20 minutes. The supernatant is saved. The upper buffy layer of the pellet is swirled off and added to the supernatant. The supernatant is centrifuged at 48,000 g (SS34, 20,000 rpm, 4° C.) for 20 minutes. The pellet is resuspended with 15 volumes of cold distilled water and centrifuged. The supernatant is discarded and the pellet is stored at −70° C.

On the day of the assay, the pellet is resuspended in 15 volumes ice-cold 50 mM Tris maleate, pH 7.4. The homogenate is preincubated with Triton-X in a final concentration of 0.04% (v/v) for 30 minutes at 37° C. with agitation. The suspension is centrifuged at 48,000 g (SS34, 20,000 rpm, 4° C.) for 20 minutes. The pellet is washed an additional 3 times by resuspension with cold buffer and centrifugation. The final pellet is resuspended in a volume 25 times the original wet weight.

C. Assay

1. Prepare assay tubes in triplicate.

| | |
|---|---|
| 380 µl | Distilled water |
| 50 µl | Buffer A, 0.5M Tris maleate, pH 7.4 |
| 20 µl | Glycine, $10^{-3}$M final concentration, or distilled water or appropriate concentration of inhibitor |
| 50 µl | [³H]Glycine, final concentration 10 nM |
| 500 µl | Tissue homogenate |
| 1000 µl | Final volume |

2. Following the addition of the tissue, the tubes are incubated for 20 minutes in an ice-bath at 0°–4° C. The binding is terminated by centrifugation (HS4, 7,000 rpm, 4° C.) for 20 minutes. The tubes are returned to ice. The supernatant is aspirated and discarded. The pellet is rinsed carefully twice with 1 ml ice-cold buffer, avoiding disruption of the pellet, and transferred to scintillation vials by vortexing the pellet with 2 ml of scintillation fluid, rinsing the tubes twice with 2 ml and then adding an additional 4 ml of scintillation fluid.

3. Specific binding is determined from the difference of binding in the absence or presence of $10^{-3}$M glycine and is typically 60–70% of total binding. $IC_{50}$ values for the competing compound are calculated by log-probit analysis of the data.

3 References:

1. Thomson, A. M. Glycine modulation of the NMDA receptor/channel complex. Trends in Neuroscience 12: 349–353, 1989.
2. Snell, L. D., Morter, R. S. and Johnson, K. M. Glycine potentiates N-methyl-D-aspartate-induced [³H]TCP binding to rat cortical membranes. Neurosci. Lett. 83: 313–317, 1987.
3. Snell, L. D., Morter, R. S. and Johnson, K. M. Structural requirements for activation of the glycine receptor that modulates the N-methyl-D-aspartate operated ion channel. Eur. J. Pharmacol. 156: 105–110, 1988.
4. Bonhaus, D. W., Yeh, G.-C., Skaryak, L. and McNamara, J. O. Glycine regulation of the N-methyl-D-aspartate receptor-gated ion channel in hippocampal membranes Mol. Pharmacol. 36: 273–279, 1989.
5. Ransom. R. Q. and Deschenes, N. L. NMDA-induced hippocampal [³H]norepinephrine release is modulated by glycine. Eur. J. Pharmacol. 156: 149–155, 1988.
6. Danysz, W., Wroblewski, J. T., Brooker, G and Costa, E. Modulation of glutamate receptors by phencyclidine and glycine in the rat cerebellum: cGMP increase in vivo. Brain Res. 479: 270–276, 1989.
7. Rao, T. S., Cler, J. A., Emmett, M. R., Mick, S. J., Iyengar, S. and Wood, P. L. Glycine, glycinamide and D-serine act as positive modulators of signal transduction at the N-methyl-D-aspartate (NMDA) receptor in vivo: differential effects on mouse cerebellar cyclic guanosine monophosphate levels. Neuropharmacol. 29: 1075–1080, 1990.
8. Oliver, M. W., Kessler, M., Larson, J., Schottler, F. and Lynch, G. Glycine site associated with the NMDA receptor modulates long-term potentiation. Synapse 5: 265–270, 1990.
9. Kishimoto, J., Simon, J. R. and Aprison, M. H. Determination of the equilibrium dissociation constants and number of glycine binding sites in several areas of the rat central nervous system, using a sodium-independent system. J. Neurochem. 37: 1015–1024, 1981.
10. Kessler, M., Terramani, T., Lynch, B. and Baudry, M. A glycine site associated with N-methyl-D-aspartic acid receptors: characterization and identification of a new class of antagonists. J. Neurochem. 52: 1319–1328, 1989.
11. Monahan, J. B., Corpus, V. M., Hood, W. F., Thomas, J. W. and Compton, R. P. Characterization of a [$^3$H]glycine recognition site as a modulatory site of the N-methyl-D-aspartate receptor complex. J. Neurochem. 53: 370–375, 1989.
12. Cotman, C. W., Monaghan, D. T., Ottersen, O. P. and Storm-Mathsen, J. Anatomical organization of excitatory amino acid receptors and their pathways. Trends in Neuroscience 10: 273–280, 1987.
13. Jansen, K. L. R., Dragunovi, M. and Faull, R. L. M. [$^3$H]Glycine binding sites, NMDA and PCP receptors have similar distributions in the human hippocampus: an autoradiographic study. Brain Res. 482: 174–178, 1989.

ENHANCEMENT OF [$^3$H]TCP BINDING

Glutamate is considered to be a major excitatory neurotransmitter in the central nervous system. In addition, glutamate has been postulated as being involved in a number of pathological conditions such as neuronal damage and loss due to ischemic stress (e.g. stroke), and in neurodegenerative disorders including Huntington's disease, amyotrophic lateral sclerosis, neurolathyrism, Alzheimer's disease and others (1,2). A central dopaminergic-glutamatergic balance was also suggested as important for both akinetic motor disorders (e.g. Parkinson's disease) and psychosis (e.g. schizophrenia)(3).

Postsynaptic effects of glutamate are mediated by a variety of glutamate receptor subtypes, which are classified as N-methyl-D-aspartate (NMDA) and non-NMDA (quisqualate, kainate) receptor subtypes. Of the glutamate receptor subtypes, the NMDA receptor has been extensively investigated. The receptor is composed of an agonist binding site (the NMDA site), and a cation channel with binding sites for magnesium and other ligands including PCP, TCP and dextromethorphan. A number of modulatory sites associated with the NMDA receptor have been identified, including binding sites for zinc, polyamines, and glycine(2). The glycine site may provide a therapeutic target for treatment of various types of cognitive impairments including Alzheimer's disease(4).

The glycine modulatory site (glycine B site) is insensitive to strychnine, whereas a strychnine sensitive glycine binding site associated with spinal cord neurons has been designated as the glycine A site. In extensively washed preparations of rat cortical membranes, NMDA increases the specific binding of [$^3$H]TCP in a concentration dependent manner ($EC_{50}$ = 3.1 μM) and addition of glycine (1 μM) potentiates the maximal effect of NMDA by a factor of 1.7(5). This preparation may be used to evaluate the effect of compounds at the NMDA associated strychnine-insensitive glycine modulatory site. Compounds can be characterized as glycine-like agonists (compounds producing an effect equivalent to the maximal effect of glycine) or glycine partial agonists (compounds producing less than the maximal effect of glycine) at this site. The prototypical glycine partial agonist is D-cycloserine(4).

Procedure(5):

Crude synaptosomal homogenates are prepared from cortical tissue obtained from male Sprague Dawley rats immediately after sacrifice or that have been frozen at –60° C. for not more than one month. Tissue is homogenized by Polytron (Brinkmann, setting 7, 60 s) in ice-cold 0.32M sucrose and centrifuged for 20 minutes at 1000 g. The resulting supernatant is decanted and recentrifuged at 17,500 g. The resulting pellet is then resuspended in 50 vols. of ice-cold distilled water and lysed at 37° C. for 30 minutes followed by centrifugation at 36,000 g for 20 minutes. The resulting pellet is carried through a second lysing and then washed by resuspension in 50 vols. of 10 mM HEPES: Na HEPES buffer (pH 7.5 at 4° C.). The homogenate is centrifuged again (36,000 g; 20 minutes), resuspended in 30 vols. of HEPES buffer and frozen at –60° C. until used for binding experiments. On the day binding is performed, the homogenate is thawed and washed three times with 30 vols. of buffer before use. There are no appreciable differences in the binding in homogenates obtained from fresh compared to frozen tissue.

All binding studies are performed by incubating homogenates (approximately 0.2 mg protein per assay tube) with 2.5 nM [$^3$H]TCP (40 Ci/mmol; New England Nuclear, Boston, Mass.) for 120 minutes at 25° C. in a final volume of 1 ml of 10 mM HEPES buffer (pH 7.5). Non-specific binding is determined in the presence of 100 μM PCP. The assay tubes were prepared in triplicate as follows:

```
360 μl  distilled water
 50 μl  0.1M HEPES buffer, pH 7.5
 20 μl  L-glutamic acid, 5 × 10⁻⁶M (Final concentration = 10⁻⁷M)
 20 μl  glycine, final concentration 10⁻⁸ to 10⁻³M, or
        compound, final concentration 10⁻⁸ to 10⁻³M,
        or distilled water, or PCP, final concentration 100 μM
 50 μl  [³H]TCP
500 μl  Tissue homogenate 1,000 μl  Final Volume
```

The binding reaction is terminated by vacuum filtration on GF/C glass fiber filters which are presoaked for 20–30 minutes in 0.05% polyethyleneimine (Sigma) in order to reduce binding to the filters. Filtration is followed by 2 washes with 4 ml of ice-cold buffer and the retained radioactivity is measured by liquid scintillation spectrometry. Protein concentration is measured by the method of Bradford (6).

Initial experiments revealed that the amount of [$^3$H]TCP binding measured varies somewhat with each membrane preparation. Therefore, in each experiment, the specific binding of [$^3$H]TCP in the absence of any additional drugs is determined and used as a basal value. This value is subtracted from the specific binding observed in the presence of added drugs. Thus, all data are expressed as the actual amount of binding above or below the basal level. Negative values indicate an inhibition of [$^3$H]TCP binding relative to this value.

TABLE II

| Compound | Displacement of [³H]Glycine Binding IC$_{50}$, μM | Enhancement of [³H]TCP Binding | |
|---|---|---|---|
| | | EC$_{50}$, μM | % maximal glycine response |
| 2-amino-N-(thieno-[2,3-b]pyridin-3-yl)-acetamide (Reference) | 21.8 | 14.4 | 39 |
| Glycine | 0.13 | 0.056 | 100 |
| D-cycloserine | 2.5 | 1.8 | 80 |

References:
1. J. W. Olney, Annu. Rev. Pharmacol. Toxicol., 30, 47–71 (1990).
2. B. A. Lawlor and K. L. Davis, Biol. Psychiatry, 31, 337–350 (1992).
3. P. Riederer et al., Arzneim.-Forsch., 42, 265–268 (1992).
4. P. T. Francis et al., Annals New York Academy of Sciences, J. H. Growdon et al., (edits.), 640, 184–188 (1991).
5. L. D. Snell et al., Neuroscience Letters, 83, 313–317 (1987).
6. M. Bradford, Anal. Biochem., 72, 248–254 (1976).

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

The following examples will further illustrate this invention but are not intended to limit it in any way. Following Table III specific illustrative preparations of compounds of the invention are described.

TABLE III

| Ex. No. | A | B | R$^1$ | R$^2$ | R$^3$ | m.p. °C. |
|---|---|---|---|---|---|---|
| 1 | CH | N | H | 4-pyridyl | H | 206–207 |
| 2 | CH | N | CH$_3$ | 4-pyridyl | H | 150–152 |
| 3 | CH | N | CH$_2$CH$_3$ | 4-pyridyl | H | 123–125 |
| 4 | CH | N | CH$_2$CH$_2$CH$_3$ | 4-pyridyl | H | 256–258 |
| 5 | CH | N | CH$_2$CH$_2$CH$_2$CH$_3$ | 4-pyridyl | H | 248–250 |
| 6 | CH | N | C(=O)CH$_2$NHCO$_2$C(CH$_3$)$_3$ | H | H | 194–196 |
| 7 | CH | N | C(=O)CH$_2$NH$_2$ | H | H | 128–129 |
| 8 | N | CH | H | 4-pyridyl | H | 236–238 |
| 9 | N | CH | CH$_3$ | 4-pyridyl | H | |
| 10 | N | CH | CH$_2$CH$_3$ | 4-pyridyl | H | |
| 11 | N | CH | CH$_2$CH$_2$CH$_3$ | 4-pyridyl | H | 119–120 |
| 12 | N | CH | CH$_2$CH$_2$CH$_2$CH$_3$ | 4-pyridyl | H | |
| 13 | N | CH | C(=O)CH$_2$NHCO$_2$C(CH$_3$)$_3$ | H | H | |
| 14 | N | CH | C(=O)CH$_2$NH$_2$ | H | H | |

EXAMPLE 1

3-(4-Pyridinylamino)thieno[2,3-b]pyridine

A solution of 3-aminothieno[2,3-b]pyridine[1,2] (9 g) and 4-chloropyridine hydrochloride (9 g) in 75 mL of 1-methyl- 2-pyrrolidinone was stirred at 90° C. for one hour. After cooling, the reaction mixture was stirred with water, washed with ether and separated. The aqueous layer was basified with 30% aqueous ammonium hydroxide and extracted with ethyl acetate. The organic extract was washed with water and saturated sodium chloride, and then was dried (anhydrous magnesium sulfate), filtered and evaporated. Elution of the residue through silica with 10% methanol in ethyl acetate via flash column chromatography afforded 6 g of a solid, m.p. 200°–204° C. Recrystallization of 2.5 g from acetonitrile afforded 2 g of a solid, m.p. 206°–207° C.

[1]L. H. Klemm, et al., J. Heterocyclic Chem., 14, 299 (1977).
[2]A. D. Dunn and R. Norrie, J. Heterocyclic Chem., 24, 85 (1987).

ANALYSIS:
Calculated for $C_{12}H_9N_3S$: 63.41% C 3.99% H 18.49% N
Found: 63.09% C 3.86% H 18.75% N

EXAMPLE 2

3-(Methyl-4-pyridinylamino)thieno[2,3-b]pyridine

A solution of 3-(4-pyridinylamino)thieno[2,3-b]pyridine (4 g) in 25 mL of dimethylformamide was added to an ice-cooled suspension of sodium hydride (60% oil dispersion, 0.85 g, washed with heptane) in 5 mL of dimethylformamide. After anion formation was completed a solution of dimethyl sulfate (2.4 g) in 5 mL of dimethylformamide was added. After one hour the reaction mixture was poured into ice-water and extracted with ethyl acetate. The organic extract was washed with water and saturated sodium chloride, and then was dried (anhydrous magnesium sulfate), filtered and evaporated to 4 g of a solid. Elution through silica with 10% methanol in ethyl acetate via flash column chromatography afforded 3 g of a solid, m.p. 143°–145° C. Recrystallization from acetonitrile afforded 2.1 g of crystals, m.p. 150°–152° C.

ANALYSIS:
Calculated for $C_{13}H_{11}N_3S$: 64.71% C 4.59% H 17.42% N
Found: 64.47% C 4.55% H 17.39% N

EXAMPLE 3

3-(Ethyl-4-pyridinylamino)thieno[2,3-b]pyridine

A solution of 3-(4-pyridinylamino)thieno[2,3-b]pyridine (4 g) in 25 mL of dimethylformamide was added to an ice-cooled suspension of sodium hydride (60% oil dispersion, 0.8 g, washed with heptane) in 5 mL of dimethylformamide. After anion formation was completed a solution of diethyl sulfate (3 g) in 5 mL of dimethylformamide was added. After one hour the reaction mixture was poured into ice-water and extracted with ethyl acetate. The organic extract was washed with water and saturated sodium chloride, and then was dried (anhydrous magnesium sulfate), filtered and evaporated to 5 g of an oil. Elution through silica with 10% methanol in ethyl acetate via flash column chromatography afforded 2.1 g of a solid. Recrystallization from acetonitrile afforded 1.4 g of crystals, m.p. 123°–125° C.

ANALYSIS:
Calculated for $C_{14}H_{13}N_3S$: 65.85% C 5.13% H 16.46% N
Found: 65.56% C 5.14% H 16.57% N

EXAMPLE 4

3-(Propyl-4-pyridinylamino)thieno[2,3-b]pyridine hydrochloride 3-(4-Pyridinylamino)thieno[2,3-b]pyridine (3 g) was added portionwise as a solid to an ice-cooled suspension of sodium hydride (60% oil dispersion, 0.8 g, washed with heptane) in 25 mL of dimethylformamide. After anion formation was completed 1-bromopropane (1.9 g) was added. After warming and stirring one hour at ambient temperature the reaction mixture was poured into ice-water and extracted with ether. The organic extract was washed with water and saturated sodium chloride then was dried (anhydrous magnesium sulfate), filtered and evaporated to 4 g of an oil. Gradient elution through silica with ethyl acetate followed by 10% methanol in ethyl acetate via flash column chromatography afforded 3.1 g of a solid, m.p. 136°–137° C. Conversion to the hydrochloride salt in 50% methanol in ether afforded 3 g of a hygroscopic solid. Recrystallization from 5% methanol in ether afforded 2.3 g of a powder, m.p. 256°–258° C.

ANALYSIS:
Calculated for $C_{15}H_{16}ClN_3S$: 58.91% C 5.27% H 13.74% N
Found: 58.69% C 5.26% H 13.61% N

EXAMPLE 5

3-(Butyl-4-pyridinylamino)thieno[2,3-b]pyridine hydrochloride

A solution of 3-(4-pyridinylamino)thieno[2,3-b]pyridine (4 g) in 25 mL of dimethylformamide was added to an ice-cooled suspension of sodium hydride (60% oil dispersion, 0.8 g, washed with heptane) in 5 mL of dimethylformamide. After anion formation was completed a solution of 1-bromobutane (2.7 g) in 5 mL of dimethylformamide was added. After one hour the reaction mixture was poured into ice-water and extracted with ethyl acetate. The organic extract was washed with water and saturated sodium chloride, and then was dried (anhydrous magnesium sulfate), filtered and evaporated. Elution through silica with 10% methanol in ethyl acetate via flash column chromatography afforded 4.2 g of an oil. Conversion to the hydrochloride salt in 10% methanol in ether afforded 3.8 g of a powder, m.p. 248°–250° C.

ANALYSIS:
Calculated for $C_{16}H_{18}ClN_3S$: 60.08% C 5.67% H 13.14% N
Found: 60.02% C 5.49% H 13.00% N

EXAMPLE 6 tert-Butyl[2-(thieno[2,3-b]pyridin-3-ylamino)-2-oxoethyl]carbamate 1,3-Dicyclohexylcarbodiimide (11 g) was added with stirring to a solution of 3-aminothieno[2,3-b]pyridine (8 g) and N-(tert-butoxycarbonyl)glycine (10 g) in 200 mL of dichloromethane. After one hour the reaction mixture was filtered to remove the separated 1,3-dicyclohexylurea and evaporated to an oil. Crystallization from ethyl ether afforded 14 g of a solid, m.p. 190°–192° C. Recrystallization of 3 g from acetonitrile afforded 2.4 g of crystals, m.p. 192°–194° C. Final recrystallization from acetonitrile afforded 2.0 g of crystals, m.p. 194°–196° C.

ANALYSIS:
Calculated for $C_{14}H_{17}N_3O_3S$: 54.71% C 5.57% H 13.67% N
Found: 55.14% C 5.84% H 13.55% N

EXAMPLE 7

2-Amino-N-(thieno[2,3-b]pyridin-3-yl)acetamide

A solution of tert-butyl[2-(thieno[2,3-b]pyridin-3-ylamino)-2-oxoethyl] carbamate (11 g) in 800 mL of methanol and 25 mL of saturated ethereal hydrogen chloride was allowed to stand at ambient temperature for twenty hours, and then was evaporated. The residue was dissolved in water, basified with 30% aqueous ammonium hydroxide and extracted with ethyl acetate. The organic extract was washed with water and saturated sodium chloride, and then was dried (anhydrous magnesium sulfate), filtered and evaporated. Gradient elution of the residue through silica with ethyl acetate and then with 20% methanol in ethyl acetate via flash column chromatography afforded 3 g of unreacted carbamate followed by 3 g of product. Trituration with ether afforded 2.5 g of a solid, m.p. 138°–139° C. Recrystallization from 10% acetonitrile in ether afforded 1.5 g of a light tan solid, m.p. 128°–129° C.

ANALYSIS:

Calculated for $C_9H_9N_3OS$: 52.15% C 4.38% H 20.28% N
Found: 51.94% C 4.32% H 20.19% N

EXAMPLE 8

3-(4-Pyridinylamino)thieno[2,3-c]pyridine

A solution of 3-aminothieno[2,3-c]pyridine (10 g) and 4-chloropyridine hydrochloride (10 g) in 200 mL of 1-methyl-2-pyrrolidinone was stirred at 80° C. for four hours, and then was cooled, stirred with ice-water, basified with sodium carbonate and extracted with ethyl acetate. The organic extract was washed with water and saturated sodium chloride, and then was dried (an hydrous magnesium sulfate), filtered and evaporated. Gradient elution through silica with dichloromethane followed by 10% methanol in dichloromethane afforded 4 g (26%) of a tan solid, m.p. 236°–238° C.

EXAMPLE 11

3-(Propyl-4-pyridinylamino)thieno[2,3-c]pyridine 3-(4-Pyridinylamino)thieno[2,3-c]pyridine (4 g) was added portionwise as a powder to a suspension of sodium hydride (60% oil dispersion, 0.8 g washed with heptane) in 50 mL of dimethylformamide. After anion formation was completed 1-bromopropane (2.2 g) was added. After stirring one hour the reaction mixture was poured into ice-water and extracted with ethyl acetate. The organic extract was washed with water saturated sodium chloride, and then was dried (anhydrous magnesium sulfate), filtered and evaporated to 5 g of a dark oil. Elution through silica with 5% methanol in ethyl acetate via flash column chromatography afforded 3.5 g of a yellow solid. Elution through alumina with ether via column chromatography afforded 2.8 g of a yellow solid. Recrystallization from heptane afforded 2.6 g (54.8%) of yellowish crystals, m.p. 119°–120° C.

ANALYSIS:

Calculated for $C_{15}H_{15}N_3S$: 66.88% C 5.61% H 15.60% N
Found: 66.78% C 5.56% H 15.52% N It should be understood that this specification and examples are set forth by way of illustration and not limitation and that various modifications and changes may be made without departing from the spirit and scope of the present invention as defined by the appended claims.

We claim:

1. A compound of the formula

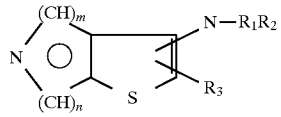

where $R^1$ is hydrogen, $(C_1-C_6)$alkyl, $(C_3-C_6)$alkenyl, $(C_3-C_6)$alkynyl, aryl$(C_1-C_6)$alkyl, $(C_1-C_6)$alkylcarbonyl, formyl, $(C_1-C_6)$alkoxycarbonyl, aryl$(C_1-C_6)$alkoxycarbonyl, aryl$(C_1-C_6)$alkoxycarbonylamino $(C_1-C_{18})$alkylcarbonyl, $(C_1-C_6)$alkoxycarbonylamino $(C_1-C_{18})$alkylcarbonyl $(C_1-C_6)$alkylamino$(C_1-C_6)$alkylcarbonyl, amino$(C_1-C_{18})$alkylcarbonyl, $(C_1-C_6)$dialkylamino$(C_1-C_6)$alkylcarbonyl, amino$(C_1-C_6)$alkyl, $(C_1-C_6)$alkylamino$(C_1-C_6)$alkyl, or $(C_1-C_6)$dialkylamino$(C_1-C_6)$alkyl;

$R^2$ is hydrogen or $(C_1-C_6)$alkyl; with the proviso that $R^1$ and $R^2$ are not concurrently hydrogen; and $R^3$ is hydrogen, $(C_1-C_6)$alkyl or $(C_1-C_6)$alkoxycarbonyl;

n is 0, 1, 2 or 3;

m is 0, 1, 2 or 3; with the proviso that the sum of m and n is always 3; and pharmaceutically acceptable addition salts thereof and optical or geometrical isomers or racemic mixtures thereof.

2. The compound of claim 1 of the formula

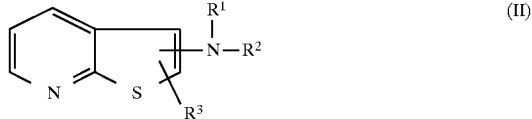

(II)

where $R^1$ is hydrogen, $(C_1-C_6)$alkyl, $(C_3-C_6)$alkenyl, $(C_3-C_6)$alkynyl, aryl$(C_1-C_6)$alkyl, aryl$(C_1-C_6)$alkoxycarbonyl, $(C_1-C_6)$alkylcarbonyl, formyl, $(C_1-C_6)$alkoxycarbonyl, $(C_1-C_6)$alkoxycarbonylamino $(C_1-C_{18})$alkylcarbonyl, aryl$(C_1-C_6)$alkoxycarbonylamino$(C_1-C_{18})$alkylcarbonyl, $(C_1-C_6)$alkylamino$(C_1-C_6)$alkylcarbonyl, amino$(C_1-C_{18})$alkylcarbonyl, $(C_1-C_6)$dialkylamino$(C_1-C_6)$alkylcarbonyl, amino$(C_1-C_6)$alkyl, $(C_1-C_6)$alkylamino$(C_1-C_6)$alkyl, or $(C_1-C_6)$dialkylamino$(C_1-C_6)$alkyl;

$R^2$ is hydrogen or $(C_1-C_6)$alkyl; with the proviso that $R^1$ and $R^2$ are not concurrently hydrogen; and $R^3$ is hydrogen, $(C_1-C_6)$alkyl or $(C_1-C_6)$alkoxycarbonyl;

pharmaceutically acceptable addition salts thereof and optical or geometrical isomers or racemic mixtures thereof.

3. The compound of claim 2 of the formula

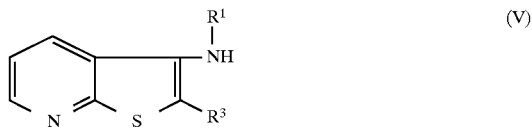

(V)

wherein $R^1$ is $(C_1-C_6)$alkoxycarbonylamino$(C_1-C_{18})$alkylcarbonyl, aryl$(C_1-C_6)$alkoxycarbonylamino $(C_1-C_{18})$alkylcarbonyl or amino$(C_1-C_{18})$alkylcarbonyl; and $R^3$ is hydrogen.

4. The compound of claim 3 wherein $R^1$ is $(C_1-C_6)$ alkoxycarbonylamino$(C_1)$alkylcarbonyl or amino$(C_1)$ alkylcarbonyl.

5. The compound of claim 4 which is 2-amino-N-(thieno [2,3-b]pyridin-3-yl)acetamide.

6. The compound of claim 4 which is t-butyl[2-(thieno [2,3-b]pyridin-3-ylamino)-2-oxoethyl]carbamate.

7. The compound of claim 1 of the formula (VI)

wherein $R^1$ is hydrogen, $(C_1-C_6)$ alkyl, $(C_3-C_6)$alkenyl, $(C_3-C_6)$ alkynyl, aryl$(C_1-C_6)$alkyl, aryl$(C_1-C_6)$ alkoxycarbonyl, $(C_1-C_6)$alkylcarbonyl, formyl, $(C_1-C_6)$alkoxycarbonyl, $(C_1-C_6)$alkoxycarbonylamino $(C_1-C_{18})$alkylcarbonyl, aryl$(C_1-C_6)$ alkoxycarbonylamino$(C_1-C_{18})$alkylcarbonyl, $(C_1-C_6)$ alkylamino-$(C_1-C_6)$alkylcarbonyl, amino$(C_1-C_{18})$ alkylcarbonyl, $(C_1-C_6)$dialkylamino-$(C_1-C_6)$ alkylcarbonyl, $(C_1-C_6)$alkoxycarbonyl, amino$(C_1-C_6)$ alkyl, $(C_1-C_6)$alkylamino$(C_1-C_6)$alkyl, or $(C_1-C_6)$ dialkylamino$(C_1-C_6)$alkyl;

$R^2$ is hydrogen or $(C_1-C_6)$alkyl; with the proviso that $R^1$ and $R^2$ are not concurrently hydrogen; and $R^3$ is hydrogen, $(C_1-C_6)$alkyl or $(C_1-C_6)$alkoxycarbonyl; and pharmaceutically acceptable acid addition salts thereof and optical or geometrical isomers or racemic mixtures thereof.

8. The compound of claim 1 of the formula (X)

wherein $R^1$ is hydrogen, $(C_1-C_6)$alkyl, $(C_3-C_6)$alkenyl, $(C_3-C_6)$ alkynyl, aryl$(C_1-C_6)$alkyl, aryl$(C_1-C_6)$ alkoxycarbonyl, $(C_1-C_6)$alkylcarbonyl, formyl, $(C_1-C_6)$alkoxycarbonyl, $(C_1-C_6)$alkoxycarbonylamino $(C_1-C_{18})$alkylcarbonyl, aryl$(C_1-C_6)$ alkoxycarbonylamino$(C_1-C_{18})$alkylcarbonyl, $(C_1-C_6)$ alkylamino$(C_1-C_6)$alkylcarbonyl, amino$(C_1-C_{18})$ alkylcarbonyl, $(C_1-C_6)$dialkylamino$(C_1-C_6)$ alkylcarbonyl, amino$(C_1-C_6)$alkyl, $(C_1-C_6)$alkylamino $(C_1-C_6)$alkyl, or $(C_1-C_6)$dialkylamino$(C_1-C_6)$alkyl;

$R^2$ is hydrogen or $(C_1-C_6)$alkyl; with the proviso that $R^1$ and $R^2$ are not concurrently hydrogen; and $R^3$ is hydrogen, $(C_1-C_6)$alkyl or $(C_1-C_6)$alkyl or $(C_1-C_6)$ alkoxycarbonyl; and pharmaceutically acceptable addition salts thereof and optical or geometrical isomers or racemic mixtures thereof.

9. The compound of claim 1 of the formula (XIV)

wherein $R^1$ is hydrogen, $(C_1-C_6)$alkyl, $(C_3-C_6)$alkenyl, $(C_3-C_6)$ alkynyl, aryl$(C_1-C_6)$alkyl, aryl$(C_1-C_6)$ alkoxycarbonyl, $(C_1-C_6)$alkylcarbonyl, formyl, $(C_1-C_6)$alkoxycarbonyl, $(C_1-C_6)$alkoxycarbonylamino $(C_1-C_{18})$alkylcarbonyl, aryl$(C_1-C_6)$ alkoxycarbonylamino$(C_1-C_{18})$alkylcarbonyl, $(C_1-C_6)$ alkylamino$(C_1-C_6)$alkylcarbonyl, amino$(C_1-C_{18})$ alkylcarbonyl, $(C_1-C_6)$dialkylamino$(C_1-C_6)$ alkylcarbonyl, amino$(C_1-C_6)$alkyl, $(C_1-C_6)$alkylamino $(C_1-C_6)$alkyl, or $(C_1-C_6)$dialkylamino$(C_1-C_6)$alkyl;

$R^2$ is hydrogen or $(C_1-C_6)$alkyl; with the proviso that $R^1$ and $R^2$ are not concurrently hydrogen; and $R^3$ is hydrogen, $(C_1-C_6)$alkyl or $(C_1-C_6)$alkoxycarbonyl; and pharmaceutically acceptable salts thereof and optical or geometrical isomers or racemic mixtures thereof.

10. The compound of claim 7 of the formula (IX)

wherein $R^1$ is $(C_1-C_6)$alkoxycarbonylamino$(C_1-C_{18})$ alkylcarbonyl, aryl$(C_1-C_6)$alkoxycarbonylamino $(C_1-C_{18})$alkylcarbonyl or amino$(C_1-C_{18})$ alkylcarbonyl; and $R^3$ is hydrogen.

11. The compound of claim 10 wherein $R^1$ is $(C_1-C_6)$ alkoxycarbonylamino$(C_1)$alkylcarbonyl or amino$(C_1)$ alkylcarbonyl.

12. The compound of claim 9 of the formula (XVII)

wherein $R^1$ is $(C_1-C_6)$alkoxycarbonylamino$(C_1-C_{18})$ alkylcarbonyl, aryl$(C_1-C_6)$alkoxycarbonylamino $(C_1-C_{18})$alkylcarbonyl or amino$(C_1-C_6)$alkylcarbonyl; and $R^3$ is hydrogen.

13. The compound of claim 12 wherein $R^1$ is $(C_1-C_6)$ alkoxycarbonylamino$(C_1)$alkylcarbonyl or amino$(C_1)$ alkylcarbonyl.

14. A pharmaceutical composition which comprises a glycine partial agonist effective amount of the compound of claim 3 and a pharmaceutically acceptable carrier.

15. A pharmaceutical composition which comprises a glycine partial agonist effective amount of the compound of claim 10 and a pharmaceutically acceptable carrier.

16. A pharmaceutical composition which comprises a glycine partial agonist effective amount of the compound of claim 12 and a pharmaceutically acceptable carrier.

17. A pharmaceutical composition which comprises a glycine partial agonist effective amount of the compound of claim 4 and a pharmaceutically acceptable carrier.

18. A method for modulating the binding of glycine associated with the N-methyl-D-aspartate receptor complex which comprises administering the compound of claim 3 in an amount effective to interact with the glycine binding site of the N-methyl-D-aspartate receptor complex.

19. A method for modulating the binding of glycine associated with the N-methyl-D-aspartate receptor complex which comprises administering the compound of claim 10 in an amount effective to interact with the glycine binding site of the N-methyl-D-aspartate receptor complex.

20. A method for modulating the binding of glycine associated with the N-methyl-D-aspartate receptor complex which comprises administering the compound of claim 4 in an amount effective to interact with the glycine binding site of the N-methyl-D-aspartate receptor complex.

21. A method for modulating the binding of glycine associated with the N-methyl-D-aspartate receptor complex which comprises administering the compound of claim 12 in an amount effective to interact with the glycine binding site of the N-methyl-D-aspartate receptor complex.

22. A method of treating a condition which is ameliorated by the use of a glycine partial agonist which comprises administering to a patient an effective amount to relieve the condition of the compound of claim 3.

23. A method of treating a condition which is ameliorated by the use of a glycine partial agonist which comprises administering to a patient an effective amount to relieve the condition of the compound of claim 10.

24. The compound of claim 8 of the formula

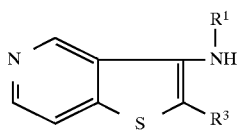

(XIII)

wherein $R^1$ is $(C_1-C_6)$alkoxycarbonylamino$(C_1-C_{18})$alkylcarbonyl, aryl$(C_1-C_6)$alkoxycarbonylamino$(C_1-C_{18})$alkylcarbonyl or amino$(C_1-C_6)$alkylcarbonyl; and $R^3$ is hydrogen.

25. The compound of claim 24 wherein $R^1$ is $(C_1-C_6)$alkoxycarbonylamino$(C_1)$alkylcarbonyl or amino$(C_1)$alkylcarbonyl.

* * * * *

UNITED STATES PATENT AND TRADEMARK OFFICE
CERTIFICATE OF CORRECTION

PATENT NO. : 5,856,335
DATED : January 5, 1999
INVENTOR(S) : Richard Charles Effland, Joseph Thomas Klein and Lawrence Leo Martin It is certified that error appears in the above-identified patent and that said Letters Patent is hereby corrected as shown below:

Column 3, Line 55 reads "$(C_1-C_6)$ or" and should read --$(C_1-C_6)$alkyl or--.

Column 3, Line 64 reads "$(C_1-C_6)$ or" and should read --$(C_1-C_6)$alkyl or--.

Column 5, Line 26 reads "Call" and should read --Class--.

Column 6, Line 46 reads "[2,3-b]" and should read --[3,2-b]--.

Column 7, Line 47 reads "dimethylacetamide" and should read --dimethylacetamide,--.

Column 9, Line 30 reads "certains" and should read --certain--.

Column 11, Line 28 reads "48,0000 g" and should read --48,000 g--.

Column 12, Line 41 reads "uptake" and should read --reuptake--.

Column 17, Line 25 reads "Dragunovi" and should read --Dragunow--.

Column 23, Line 31 reads "(an hydrous" and should read --(anhydrous--.

Signed and Sealed this

Seventeenth Day of April, 2001

Attest:

NICHOLAS P. GODICI

Attesting Officer    Acting Director of the United States Patent and Trademark Office